United States Patent
Toellner et al.

(10) Patent No.: US 10,709,828 B2
(45) Date of Patent: *Jul. 14, 2020

(54) SHEATH DEVICE FOR INSERTING A CATHETER

(71) Applicant: ECP ENTWICKLUNGSGESELLSCHAFT MBH, Berlin (DE)

(72) Inventors: Thomas Toellner, Berlin (DE); Robert Decke, Berlin (DE)

(73) Assignee: ECP ENTWICKLUNGSGESELLSCHAFT MBH, Berlin (DE)

( * ) Notice: Subject to any disclaimer, the term of this patent is extended or adjusted under 35 U.S.C. 154(b) by 613 days.

This patent is subject to a terminal disclaimer.

(21) Appl. No.: 13/261,918

(22) PCT Filed: Dec. 21, 2012

(86) PCT No.: PCT/EP2012/076770
§ 371 (c)(1),
(2) Date: Jun. 17, 2014

(87) PCT Pub. No.: WO2013/093058
PCT Pub. Date: Jun. 27, 2013

(65) Prior Publication Data
US 2015/0141738 A1 May 21, 2015

Related U.S. Application Data

(60) Provisional application No. 61/579,163, filed on Dec. 22, 2011.

(30) Foreign Application Priority Data

Dec. 22, 2011 (EP) .................................... 11075273

(51) Int. Cl.
*A61M 1/10* (2006.01)
*A61M 25/06* (2006.01)
(Continued)

(52) U.S. Cl.
CPC .......... *A61M 1/1024* (2014.02); *A61M 1/122* (2014.02); *A61M 25/0662* (2013.01);
(Continued)

(58) Field of Classification Search
CPC ................ A61M 1/1024; A61M 1/122; A61M 25/0097; A61M 25/0662; A61M 39/06; A61M 39/0613; A61B 2017/00469
(Continued)

(56) References Cited

U.S. PATENT DOCUMENTS 2,350,534 A 6/1944 Rosinger
3,333,127 A 7/1967 Congdon et al.
(Continued)

FOREIGN PATENT DOCUMENTS

CA 2613175 A1 1/2007
CA 2632420 A1 6/2007
(Continued)

OTHER PUBLICATIONS

Brochure Impella Pumpsystem of Impella CardioSystems AG, "Turning Lives Around," Aug. 2003 (4 pages).
(Continued)

*Primary Examiner* — Gary Jackson
*Assistant Examiner* — Pamela M. Bays
(74) *Attorney, Agent, or Firm* — Botos Churchill IP Law LLP

(57) ABSTRACT

A sheath device for inserting a catheter into a patient's body is described. The device has a first sheath with a proximal end and a distal end. When the device is used as intended, the distal end of the first sheath is provided for arrangement
(Continued)

in the patient's body and the proximal end of the first sheath is provided for arrangement outside the patient's body. The first sheath comprises a tubular section and a sheath housing, which is disposed at the proximal end of the section and has a receiving channel for a strand-shaped body. The device solves the problem of reliably fixing a second sheath or a catheter with respect to the first sheath by providing a clamping element on the receiving channel for fixing a strand-shaped body in the receiving channel by way of clamping.

20 Claims, 10 Drawing Sheets

(51) Int. Cl.
    *A61M 39/06*     (2006.01)
    *A61M 1/12*     (2006.01)
    *A61B 17/00*     (2006.01)
    *A61M 25/00*     (2006.01)

(52) U.S. Cl.
    CPC ........ *A61M 39/06* (2013.01); *A61M 39/0613* (2013.01); *A61B 2017/00469* (2013.01); *A61M 1/101* (2013.01); *A61M 1/1008* (2014.02); *A61M 1/1034* (2014.02); *A61M 1/12* (2013.01); *A61M 1/125* (2014.02); *A61M 25/0097* (2013.01); *A61M 2025/0681* (2013.01); *A61M 2039/062* (2013.01); *A61M 2039/0633* (2013.01)

(58) Field of Classification Search
    USPC .......................................................... 600/16
    See application file for complete search history.

(56) References Cited

U.S. PATENT DOCUMENTS

| | | |
|---|---|---|
| 3,354,833 A | 11/1967 | Laing |
| 3,489,145 A | 1/1970 | Judson et al. |
| 3,936,683 A | 2/1976 | Walker |
| 4,065,234 A | 12/1977 | Yoshiyuki et al. |
| 4,115,040 A | 9/1978 | Knorr |
| 4,135,253 A | 1/1979 | Reich et al. |
| 4,153,048 A | 5/1979 | Magrini |
| 4,420,851 A | 12/1983 | Wiener |
| 4,610,674 A * | 9/1986 | Suzuki ............... A61M 25/0662 604/528 |
| 4,679,558 A | 7/1987 | Kensey et al. |
| 4,686,982 A | 8/1987 | Nash |
| 4,699,611 A | 10/1987 | Bowden |
| 4,728,319 A | 3/1988 | Masch |
| 4,747,821 A | 5/1988 | Kensey et al. |
| 4,747,840 A | 5/1988 | Ladika et al. |
| 4,749,376 A | 6/1988 | Kensey et al. |
| 4,753,221 A | 6/1988 | Kensey et al. |
| 4,777,951 A | 10/1988 | Cribier et al. |
| 4,846,152 A | 7/1989 | Wampler et al. |
| 4,895,557 A | 1/1990 | Moise et al. |
| 4,919,647 A | 4/1990 | Nash |
| 4,984,972 A | 1/1991 | Clausen et al. |
| 5,011,469 A | 4/1991 | Buckberg et al. |
| 5,017,103 A | 5/1991 | Dahl |
| 5,037,403 A | 8/1991 | Garcia |
| 5,042,984 A | 8/1991 | Kensey et al. |
| 5,061,256 A | 10/1991 | Wampler |
| 5,097,849 A | 3/1992 | Kensey et al. |
| 5,139,486 A | 8/1992 | Moss |
| 5,147,186 A | 9/1992 | Buckholtz |
| 5,158,279 A | 10/1992 | Laffey et al. |
| 5,163,431 A | 11/1992 | Griep |
| 5,167,636 A | 12/1992 | Clement |
| 5,169,378 A | 12/1992 | Figuera |
| 5,234,425 A | 8/1993 | Fogarty et al. |
| 5,250,059 A | 10/1993 | Andreas et al. |
| 5,275,580 A | 1/1994 | Yamazaki |
| 5,282,790 A | 2/1994 | Clement |
| 5,304,142 A | 4/1994 | Liebl et al. |
| 5,320,611 A | 6/1994 | Bonutti et al. |
| 5,357,963 A | 10/1994 | Mayol et al. |
| 5,376,114 A | 12/1994 | Jarvik |
| 5,395,341 A | 3/1995 | Slater |
| 5,397,310 A | 3/1995 | Chu et al. |
| 5,405,383 A | 4/1995 | Barr |
| 5,407,430 A | 4/1995 | Peters |
| 5,421,338 A | 6/1995 | Crowley et al. |
| 5,480,392 A | 1/1996 | Mous |
| 5,488,960 A | 2/1996 | Toner |
| 5,492,530 A | 2/1996 | Fischell et al. |
| 5,533,986 A | 7/1996 | Mottola et al. |
| 5,536,255 A | 7/1996 | Moss |
| 5,573,517 A | 11/1996 | Bonutti et al. |
| 5,653,697 A | 8/1997 | Quiachon et al. |
| 5,749,855 A | 5/1998 | Reitan |
| 5,827,171 A | 10/1998 | Dobak, III et al. |
| 5,863,179 A | 1/1999 | Westphal et al. |
| 5,888,241 A | 3/1999 | Jarvik |
| 5,911,702 A | 6/1999 | Romley et al. |
| 5,935,122 A | 8/1999 | Fourkas et al. |
| 5,938,672 A | 8/1999 | Nash |
| 5,954,745 A | 9/1999 | Gertler et al. |
| 5,971,993 A | 10/1999 | Hussein et al. |
| 5,984,944 A | 11/1999 | Forber |
| 6,001,078 A | 12/1999 | Reekers |
| 6,054,788 A | 4/2000 | Dombrovski et al. |
| 6,083,260 A | 7/2000 | Aboul-Hosn |
| 6,123,725 A | 9/2000 | Aboul-Hosn |
| 6,129,704 A | 10/2000 | Forman et al. |
| 6,183,220 B1 | 2/2001 | Ohara et al. |
| 6,197,016 B1 | 3/2001 | Fourkas et al. |
| 6,245,007 B1 | 6/2001 | Bedingham et al. |
| 6,338,730 B1 | 1/2002 | Bonutti et al. |
| 6,350,278 B1 | 2/2002 | Lenker et al. |
| 6,413,222 B1 | 7/2002 | Pantages et al. |
| 6,428,556 B1 | 8/2002 | Chin |
| 6,517,528 B1 | 2/2003 | Pantages et al. |
| 6,533,716 B1 | 3/2003 | Schmitz-Rode et al. |
| 6,537,247 B2 | 3/2003 | Shannon |
| 6,540,712 B1 | 4/2003 | Parodi et al. |
| 6,544,216 B1 | 4/2003 | Sammler et al. |
| 6,613,038 B2 | 9/2003 | Bonutti et al. |
| 6,656,153 B1 | 12/2003 | Sakai et al. |
| 6,692,462 B2 | 2/2004 | Mackenzie et al. |
| 6,814,715 B2 | 11/2004 | Bonutti et al. |
| 6,841,910 B2 | 1/2005 | Gery |
| 6,858,001 B1 | 2/2005 | Aboul-Hosn |
| 6,974,436 B1 | 12/2005 | Aboul-Hosn et al. |
| 6,976,996 B1 | 12/2005 | Aboul-Hosn |
| 6,981,942 B2 | 1/2006 | Khaw et al. |
| 7,022,100 B1 | 4/2006 | Aboul-Hosn et al. |
| 7,025,746 B2 | 4/2006 | Tal |
| 7,027,875 B2 | 4/2006 | Siess et al. |
| 7,166,088 B2 | 1/2007 | Heuser |
| 7,393,181 B2 | 7/2008 | McBride et al. |
| 7,632,254 B1 | 12/2009 | Bjorkman et al. |
| 7,646,376 B2 | 1/2010 | Blersch |
| 7,722,567 B2 | 5/2010 | Tal |
| 7,731,675 B2 | 6/2010 | Aboul-Hosn et al. |
| 7,841,976 B2 | 11/2010 | McBride et al. |
| 7,914,492 B2 | 3/2011 | Heuser |
| 7,927,068 B2 | 4/2011 | McBride et al. |
| 8,066,674 B2 | 11/2011 | Heuser |
| 8,079,948 B2 | 12/2011 | Shifflette |
| 3,439,859 A1 | 5/2013 | Pfeffer et al. |
| 8,597,277 B2 | 12/2013 | Lenker et al. |
| 8,672,888 B2 | 3/2014 | Tal |
| 8,758,402 B2 | 6/2014 | Jenson et al. |
| 8,888,728 B2 | 11/2014 | Aboul-Hosn et al. |
| 9,623,228 B2 | 4/2017 | Ryan et al. |
| 2001/0000528 A1 | 4/2001 | Cho |
| 2002/0120226 A1 | 8/2002 | Beck |
| 2002/0151799 A1 | 10/2002 | Pantages et al. |

(56) References Cited

U.S. PATENT DOCUMENTS

| | | |
|---|---|---|
| 2003/0135940 A1 | 7/2003 | Lev et al. |
| 2003/0208097 A1 | 11/2003 | Aboul-Hosn et al. |
| 2004/0022640 A1 | 2/2004 | Siess et al. |
| 2004/0044266 A1 | 3/2004 | Siess et al. |
| 2004/0113502 A1 | 6/2004 | Li et al. |
| 2004/0147877 A1* | 7/2004 | Heuser .............. A61M 25/0662 604/165.02 |
| 2004/0193046 A1 | 9/2004 | Nash et al. |
| 2004/0230287 A1 | 11/2004 | Hartley et al. |
| 2004/0260237 A1 | 12/2004 | Squadrito |
| 2005/0135942 A1 | 6/2005 | Wood et al. |
| 2005/0149097 A1 | 7/2005 | Regnell et al. |
| 2005/0149105 A1 | 7/2005 | Leeflang et al. |
| 2005/0245892 A1 | 11/2005 | Elkins et al. |
| 2006/0008349 A1 | 1/2006 | Khaw |
| 2006/0062672 A1 | 3/2006 | McBride et al. |
| 2006/0135981 A1 | 6/2006 | Lenker et al. |
| 2006/0195004 A1 | 8/2006 | Jarvik |
| 2006/0287574 A1 | 12/2006 | Chin |
| 2007/0118072 A1 | 5/2007 | Nash |
| 2007/0299499 A1 | 12/2007 | Hartley et al. |
| 2008/0004569 A1 | 1/2008 | McCrystle et al. |
| 2008/0004571 A1 | 1/2008 | Voss |
| 2008/0033396 A1* | 2/2008 | Danek ............... A61M 25/0662 604/508 |
| 2008/0046005 A1 | 2/2008 | Lenker et al. |
| 2008/0051734 A1 | 2/2008 | Bonutti et al. |
| 2008/0051821 A1 | 2/2008 | Gephart |
| 2008/0065011 A1 | 3/2008 | Marchand et al. |
| 2008/0082165 A1 | 4/2008 | Wilson et al. |
| 2008/0097386 A1 | 4/2008 | Osypka |
| 2008/0103591 A1 | 5/2008 | Siess |
| 2008/0114339 A1 | 5/2008 | McBride et al. |
| 2008/0132747 A1 | 6/2008 | Shifflette |
| 2008/0177249 A1 | 7/2008 | Heuser et al. |
| 2008/0183136 A1 | 7/2008 | Lenker et al. |
| 2008/0319387 A1 | 12/2008 | Amisar et al. |
| 2009/0012476 A1 | 1/2009 | Catlin |
| 2009/0024201 A1 | 1/2009 | Fitzgerald et al. |
| 2009/0060743 A1 | 3/2009 | McBride et al. |
| 2009/0062597 A1 | 3/2009 | Shifflette |
| 2009/0088609 A1 | 4/2009 | Schmitz-Rode et al. |
| 2009/0093764 A1 | 4/2009 | Pfeffer et al. |
| 2009/0093796 A1 | 4/2009 | Pfeffer et al. |
| 2009/0218728 A1 | 9/2009 | Moyer |
| 2009/0227892 A1 | 9/2009 | Krombach et al. |
| 2009/0240202 A1 | 9/2009 | Drasler et al. |
| 2010/0004730 A1 | 1/2010 | Benjamin et al. |
| 2010/0030161 A1* | 2/2010 | Duffy ................ A61M 25/0668 604/246 |
| 2010/0160863 A1 | 6/2010 | Heuser |
| 2010/0210895 A1 | 8/2010 | Aboul-Hosn et al. |
| 2010/0268017 A1 | 10/2010 | Siess |
| 2011/0071338 A1 | 3/2011 | McBride et al. |
| 2013/0035628 A1 | 2/2013 | Garrison et al. |
| 2013/0041202 A1 | 2/2013 | Toellner |
| 2013/0066140 A1 | 3/2013 | McBride et al. |
| 2013/0131718 A1 | 5/2013 | Jenson et al. |
| 2013/0197621 A1 | 8/2013 | Ryan et al. |
| 2013/0317438 A1 | 11/2013 | Ellingwood et al. |
| 2013/0317481 A1 | 11/2013 | Ellingwood et al. |
| 2014/0018732 A1* | 1/2014 | Bagaoisan ........ A61M 25/0136 604/95.04 |
| 2015/0073202 A1 | 3/2015 | Aboul-Hosn et al. |
| 2016/0066948 A1 | 3/2016 | Ellingwood et al. |
| 2016/0220358 A1 | 8/2016 | Wilson et al. |
| 2016/0354583 A1 | 12/2016 | Ellingwood et al. |
| 2017/0056063 A1 | 3/2017 | Ellingwood et al. |
| 2017/0281908 A1 | 10/2017 | Ellingwood et al. |

FOREIGN PATENT DOCUMENTS

| | | |
|---|---|---|
| CA | 2701810 A1 | 4/2009 |
| DE | 4414903 A1 | 11/1995 |
| DE | 29804046 U1 | 4/1998 |
| DE | 10059714 C1 | 5/2002 |
| DE | 102005039950 A1 | 3/2007 |
| EP | 0364293 A2 | 4/1990 |
| EP | 0445782 A1 | 9/1991 |
| EP | 0768900 A1 | 4/1997 |
| EP | 914171 A2 | 5/1999 |
| EP | 0916359 A1 | 5/1999 |
| EP | 1034808 A1 | 9/2000 |
| EP | 1207934 A2 | 5/2002 |
| EP | 2047872 B1 | 9/2010 |
| EP | 2229965 A1 | 9/2010 |
| EP | 2347778 A1 | 7/2011 |
| EP | 2399639 | 12/2011 |
| FR | 2788223 A1 | 7/2000 |
| JP | H04126158 A | 4/1992 |
| WO | WO-9944651 A1 | 9/1999 |
| WO | WO-9958170 A1 | 11/1999 |
| WO | WO-2000019097 A1 | 4/2000 |
| WO | WO-2000043053 A1 | 7/2000 |
| WO | WO-2001083016 A2 | 11/2001 |
| WO | WO-2002022200 A1 | 3/2002 |
| WO | 02/43791 A1 | 6/2002 |
| WO | WO-2003103745 A2 | 12/2003 |
| WO | WO-2006020942 A1 | 2/2006 |
| WO | WO-2006034158 A2 | 3/2006 |
| WO | WO-2010/063494 A1 | 6/2010 |
| WO | WO-2011089022 A1 | 7/2011 |
| WO | 2011/115048 A1 | 9/2011 |

OTHER PUBLICATIONS

Buecker A et al., "Use of a Nonmetallic Guide Wire for Magnetic Resonance—Guided Coronary Artery Catheterization," Investigative Radiology, 39:11, pp. 656-660 (2004).

Compendium of Technical and Scientific Information for the Hemopump Temporary Cardiac Assist System, 1988 (15 pages).

Dekker, Andre, et al, "Efficacy of a New Intraaortic Propeller Pump vs the Intraaortic Balloon Pump," Chest Journal; Jun. 2003 (7 pages).

Frazier, O.H., et al, "First Human Use of the Hemopump, A Cather-Mounted Ventricular Assist Device," Ann Thorac Surg., Feb.; 49(2): pp. 299-304 (1990).

International Preliminary Report on Patentability, from PCT/EP09/008858, dated Jun. 7, 2011.

JOMED Reitan Catheter Pump Brochure, www.jomed.com/rcp (undated) (6 pages).

Lueger, Lexikon der Technik, "Lexikon der Feinwerktechnik", vol. 13, Deutsche Verlags-Anstalt GmbH, Stuttgart, seite 551 (1968).

Reitan, Oyvind et al, "Hydrodynamic Properties of a New Percutaneous Intra-aortic Axial Flow Pump," ASAIO Journal; May-Jun.; vol. 16; pp. 323-329 (2000).

Rothman, Martin T, "The Reitan Catheter Pump: A New Versatile Approach for Hemodynamic Support," London Chest Hospital Barts & The Long NHS Trust, presented at TCT Conference, Oct. 24-26, 2006, (40 pages).

Schmitz-Rode, T et al, "Temporary Pulmonary Stent Placement as Emergency Treatment of Pulmonary Embolism," Journal of the American College of Cardiology, 48:4, pp. 812-816 (2006).

Schmitz-Rode, T et al., "An Expandable Percutaneous Catheter Pump for Left Ventricular Support," Journal of the American College of Cardiology, 45:11, pp. 1856-1861 (2005).

Siess, Thorsten, "Systemanalyse and Entwicklung intravasaler Rotationspumpen zur Herzunterstutzung," Helmholtz-Institut, Jun. 24, 1998 (105 pages) and partial English translation (37 pages).

Verma, R et al., "Evaluation of a Newly Developed Percutaneous Thrombectomy Basket Device in Sheep with Central Pulmonary Embolisms," Investigative Radiology, 41:10, pp. 729-734 (2006).

Wampler, Richard, K., "In Vivo Evaluation of a Peripheral Vascular Access Axial Flow Blood Pump," ASAIO Trans., Jul.-Sep.;34(3): pp. 450-454 (1988).

* cited by examiner

SHEATH DEVICE FOR INSERTING A CATHETER

RELATED APPLICATIONS

This application is a national stage entry under 35 U.S.C. § 371 of International Application No. PCT/EP2012/076770, filed Dec. 21, 2012, which claims the benefit of priority from U.S. Provisional Application No. 61/579,163, filed Dec. 22, 2011 (now expired) and European Patent Application No. 11075273.0 filed Dec. 22, 2011. The specifications of each of the foregoing applications are incorporated herein by reference in their entirety.

BACKGROUND OF THE INVENTION

The invention resides in the mechanical field, and more particularly in the medical engineering field, and relates to a sheath device for inserting a catheter into a patient's body.

Especially in microinvasive or minimally invasive applications in the medical field, functional elements such as stents, milling heads for clearing blood vessels by milling, or cardiac support pumps, are frequently inserted into the interior of a patient's body, specifically into endogenous vessels, and more particularly blood vessels, through an opening by means of catheters. So as to be able to insert such catheters once or several times while minimizing the traumatization of the affected tissue, and also while minimizing the risk of damage to the sensitive medical devices, sheaths are frequently employed, which are permanently or temporarily introduced in a patient's body and which have an inner lumen, which allows a catheter or other functional elements to be guided through. The Seldinger Technique, which will be described in more detail below in connection with FIG. 1, is known for inserting such a sheath into the patient's body.

A corresponding method is known from WO 02/43791 A1, for example.

Once such a sheath is installed, it can be used permanently or repeatedly for inserting and removing a catheter.

A special application lies in the use of such a sheath for compressible blood pumps or other functional elements, which are first compressed, notably radially compressed, so as to allow better introduction into the body, and then inserted in the compressed state through the sheath to the site of use or to the vicinity of the site of use, whereupon they are expanded. For this purpose, corresponding blood pumps are known, which comprise a pump head at the distal end of a hollow catheter, wherein the pump head comprises a rotor having radially expandable delivery blades and a likewise compressible and expandable housing. The corresponding elements are designed so that they expand automatically, for example if they have been previously elastically compressed, or that they are expanded at the start of a rotary operation by the resistance of the liquid to be delivered, such as the blood (this applies in particular to delivery blades of the rotor).

Other effects, such as shape memory effects in what are known as shape memory alloys, such as nitinol, can, for example, also be used for the purpose of a subsequent shape change.

Corresponding compressible blood pumps are known from WO 02/43791 A1 or from EP 2 047 872 A1, and from DE 100 59 714, for example.

To allow better introduction, such blood pumps or other functional element can advantageously be precompressed by means of an aforementioned sheath and can be kept available, for example in a second sheath, for the treatment of a patient before insertion into the first sheath. The second sheath is then designed such that the functional element, notably the pump head, is held in a compressed state in the interior of the sheath (lumen), for example in the same diameter which is also required for insertion into the first sheath, or slightly larger. So as to transfer the pump from the second sheath into the first sheath, the two sheaths are then typically coupled such that they are coupled coaxially relative to each other at the smallest possible distance from each other, so as to axially displace the pump out of the second sheath and into the first sheath.

This procedure is critical because all components, and the catheter, the pump head and the second sheath in particular, are subjected to high mechanical stress. In addition, it is a problem that under surgery conditions this sheath process must generally be carried out manually using few other aids, placing high demands on the simplicity of the process and on the reliability.

BRIEF SUMMARY OF THE INVENTION

Against this background, it is the object of the present invention to create a sheath device of the type mentioned above, which allows a functional element to be inserted into the patient's body with high reliability, low sensitivity, low design complexity and low risk of injury to the patient and damage to the medical devices.

The object is achieved by the features of the invention according to claims 1 and 10 and by a method according to claim 12.

According to the invention, a sheath device for inserting a catheter into a patient's body is created, comprising a first sheath, the proximal end of which is provided for arrangement outside the patient's body when used as intended, while the distal end of the first sheath is located inside the patient's body during use. The first sheath comprises a tubular section and a sheath housing, which is disposed at the proximal end of the section and has a receiving channel for a strand-shaped body, and more particularly for a catheter and/or a second sheath.

By providing a clamping element on the receiving channel, the strand-shaped body, and more particularly the catheter and/or a sheath, can be clamped into the receiving channel. When a functional element, notably a pump, is precompressed at the end of a catheter in a second sheath, this second sheath can be inserted into the sheath housing and fixed there by means of the clamping element. The second sheath and the first sheath can thus be oriented coaxially relative to one another and axially fixed with respect to one another at a desired relative distance, so that the catheter, together with the functional element, can be pushed from the second sheath into the first sheath.

The term "clamping" as used in the context of the present application means a releasable joint, notably a force-fit and/or frictional engagement, of an object within the receiving channel, but also any kind of joint wherein a strand-like, tubular or hose-like body is releasably secured and/or coaxially guided with respect to the receiving channel. Examples of these joints include a threaded joint, a bayonet joint, a sealing conical joint (Luer joint), optionally in combination with a threaded or bayonet joint (Luer lock), or a threaded joint which, upon application of a surplus axial force, allows a relative axial movement of thread mates via a radial, notably elastic deformation of said mates, in order to establish or to release said clamped joint. As an alternative, said clamping mates may also be provided with circumferential beads or annular grooves on their respective opposite lateral walls to allow their mutual engagement.

The wall thickness and the material of the second sheath are selected such that the second sheath can be clamped into the clamping element without the catheter also being clamped in the second sheath. The design of the second sheath is so stable that it is compressed only insignificantly during clamping. The wall thickness of the hollow-cylindrical second sheath can advantageously range between 0.2 and 1.0 mm, and more particularly between 0.3 and 0.7 mm.

This also creates the option of removing the second sheath after the clamping element has been released, following the insertion of the catheter and/or the functional element into the first sheath, and of designing it as a peel-away sheath, for example, so that it can be removed by tearing it open, with the catheter remaining in the receiving channel. Despite the smaller diameter, the catheter can be clamped in the clamping element so as to fix the functional element in the patient's body with respect to the first sheath. A certain time after insertion, after the mechanical parts have settled and taken on the patient's body temperature, readjustment may be necessary, and the clamping element can be released again, the catheter can be readjusted and the clamping element can be re-fixed. As an alternative, it is also possible to fix the catheter in a further clamping element which is matched to the smaller diameter.

According to an advantageous embodiment of the invention, the clamping element comprises an elastically radially deformable clamping ring. Such a radially deformable clamping ring is a very simple and cost-effective way of creating a clamping element which allows reliable clamping, without the risk of damaging a second sheath or a catheter. The clamping ring can advantageously be produced from an elastomer and the volume thereof can be incompressible, so that it radially expands during axial compression. However, it can also be composed of a foamed material, in which some of the volume can be compressed, but which likewise radially expands during axial compression.

In addition, it is possible for the clamping ring to be produced from a plastic material or metal and to be slotted. Such a clamping ring can, for example, have a conical shape on the outside, so as to be radially compressible by the axial movement of a further ring designed as a clamping cone.

The invention can advantageously be such that the clamping ring can be expanded radially inward by means of a screw element acting axially relative to the receiving channel. Under surgery conditions, such a screw element can be used, for example by means of a screw wheel having a diameter that can also be greater than that of the sheath housing, to compress a clamping ring in a simple manner, and thus clamp the second sheath or the catheter.

When using a pressure piece having a wedge-shaped cylindrical cross-section, the Invention can be attained by radially inwardly compressing the clamping ring by means of the axially acting screw element and an axially movable wedge body, notably a ring having a wedge-shaped cross-section.

So as to minimize the penetration of microbes into the patient's body through the first sheath both when inserting a second sheath and a catheter and later, during operation, it is further possible for a radial expansion of the receiving channel to be provided on the side of the clamping ring located opposite the pressure piece or wedge body, as seen looking in the axial direction, the radial expansion comprising a flushing element.

For the same purpose, and additionally so as to prevent body fluids, notably blood, from exiting through the sheath, according to the invention a valve sealing the receiving channel may be disposed in the flushing space, and more particularly on the side of the clamping ring located opposite the pressure piece or the wedge body, as seen looking in the axial direction. Such a valve can, for example, be designed as a dual valve comprising a plate valve and a dome valve, wherein the plate valve provides optimal sealing action if no catheter and/or no second sheath extends through the receiving channel, whereby the plate valve as a whole can be held in a closed state. If a catheter or another strand-shaped body is pushed through, the dome valve, which can, for example, take on the geometric shape of a spherical cap, allows optimal sealing around the strand-shaped body. However, different designs of the valve are also possible to fulfill the aforementioned sealing functions.

In addition to a sheath device of the type mentioned above, the invention further relates to a catheter device comprising a corresponding sheath device and comprising a catheter, which extends through the receiving channel and is fixed in the clamping element.

The invention further relates to a catheter device comprising a sheath device, as that which is described above, and a catheter and further comprising a second sleeve-shaped sheath, which surrounds the catheter and extends through the receiving channel, the sleeve-shaped second sheath being fixed in the clamping element.

In addition to a sheath device and a catheter device of the types described above, the invention also relates to a method for inserting a catheter into a patient's body by means of a sheath device according to any one of the variants described above and comprising a second sheath, wherein the second sheath is first inserted together with the catheter into the first sheath, and more particularly to a mechanical stop, and wherein the second sheath is thereafter fixed by means of the clamping element and the catheter is then transferred from the second sheath into the first sheath.

According to an advantageous embodiment of the method according to the invention, the second sheath is removed, in particular by tearing it open or off, after the catheter has been inserted into the first sheath.

The method according to the invention can advantageously provide for the catheter to be directly fixed in the clamping element after the second sheath has been removed.

BRIEF DESCRIPTION OF THE DRAWINGS

The invention will be shown in drawings and then described hereafter based on an exemplary embodiment. In the drawings.

DETAILED DESCRIPTION OF THE INVENTION

Figure 1:
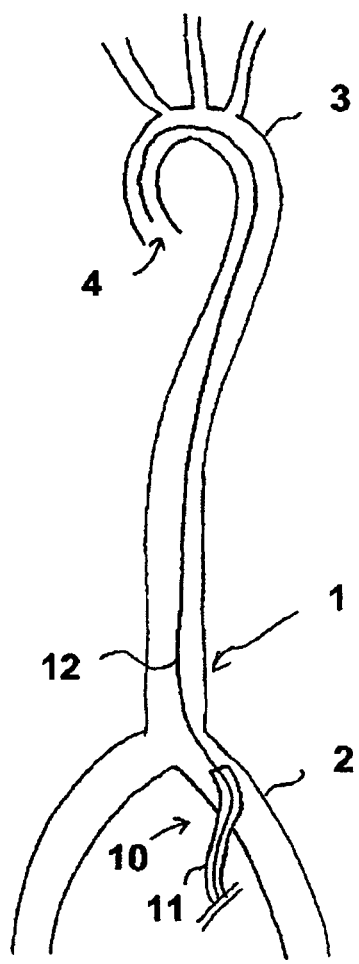
FIG. 1 is a schematic overview of a vascular system comprising an inserted first sheath.

The sterile hose part 130 is fluid tight and tightly connected to the sheath device 101 that may be a first sheath device according to the invention. The sterile hose part may be fixed to a first and/or second sheath device by one of the clamping/fixing means 131 disclosed in the FIGS. 1-13i. The sterile hose part may be directly fixed to a housing of one of the sheath devices.

The second sheath device is at least partially positioned in the sterile hose part and after insertion of a catheter into the body of a patient, the second sheath device, if e.g. made as a peel-away sheath, may be torn away and disposed in the second sheath. In this case, the first sheath device can be tightly separated from the sterile hose part and the proximal end of the sterile hose part can be tightly clamped on the catheter itself proximally to the remaining parts of the sterile hose part.

The sterile hose part may, after use, be axially compressed and an end flange 132 of the hose part may be fixed to fixing means 131 which may also form an end flange of the hose part.

Before removal of the second sheath device, circumferential openings 119 in the second sheath device which are positioned inside the housing of the first sheath device allow for flushing of the inside of the second sheath device together with the inside of the first sheath device.

FIG. 1 shows a schematic human vascular system 1. One of the femoral arteries 2 is located in the groin region and is connected to the aortic arch 3 via an aorta and then leads into the ventricle 4. An introducer sheath 10 is first inserted into the femoral artery 2, for example using the Seldinger Technique. The femoral artery, or any blood vessel, is punctured for this purpose, for example using a steel cannula having a cutting tip. A guide wire 12 is pushed through the steel cannula, which is inserted into the puncture site, and inserted into the left ventricle 4 retrogradely via the aortic arch 3.

After the puncturing cannula is removed, the first sheath 10, which is designed as an introducer sheath and comprises a tubular section 11 and optionally a dilator, which is not shown here, is threaded on the guide wire and inserted into the vascular system through the punctured site, wherein the sheath is inserted a short distance into the lumen of the vascular system or even to the site of use of an element to be inserted. Thereafter, a fluid pump is inserted into the vascular system through the introducer sheath 10.

The tubular section 11 of the first sheath 10 is inserted into the artery such that the proximal end of the first sheath 10 is located outside the femoral artery and can thus be used for inserting a pump, for example. It is thus possible to thread the pump on the guide wire 12 so as to guide the pump into the left ventricle by means of the guide wire.

It is also possible to guide the tubular section 11 of the first sheath 10 through the guide wire into the left ventricle and to then remove the guide wire 12 from the first sheath. A pump unit that may be present is then guided through the first sheath volume into the vicinity of or into the left ventricle 4.

In the present example, the method is only illustrated based on the insertion of a pump into the left ventricle so as support a cardiac function. However, it is easy to see for a person skilled in the art that the pump, or another functional element, can also be disposed and introduced in other regions of the endogenous vascular system.

Figure 2:
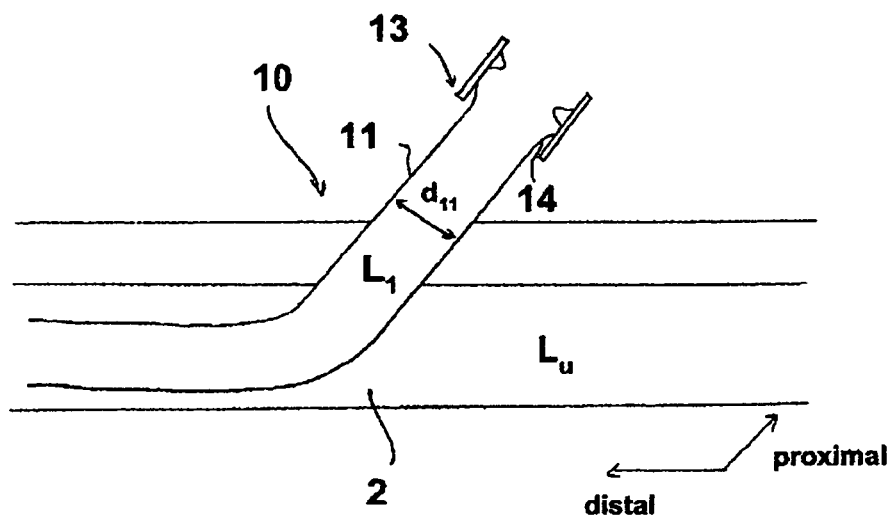
FIG. 2 is a detailed view of a section of FIG. 1.

FIG. 2 shows the region of FIG. 1 in which the first sheath 10 is guided from outside through the endogenous tissue into the lumen LG of the femoral artery 2. The first sheath comprises a tubular section 11, which is connected to a sheath housing 13 at the proximal end. The tubular section 11 defines a lumen L1, which has an inside diameter d11. This inside diameter widens toward the proximal end of the tubular section 11 in a trumpet-like shape in the region 14.

The sheath housing 13 contains a haemostatic valve, which is known from the prior art. This valve prevents fluid present in the lumen LG from exiting to the outside through the lumen L1.

Figure 3:
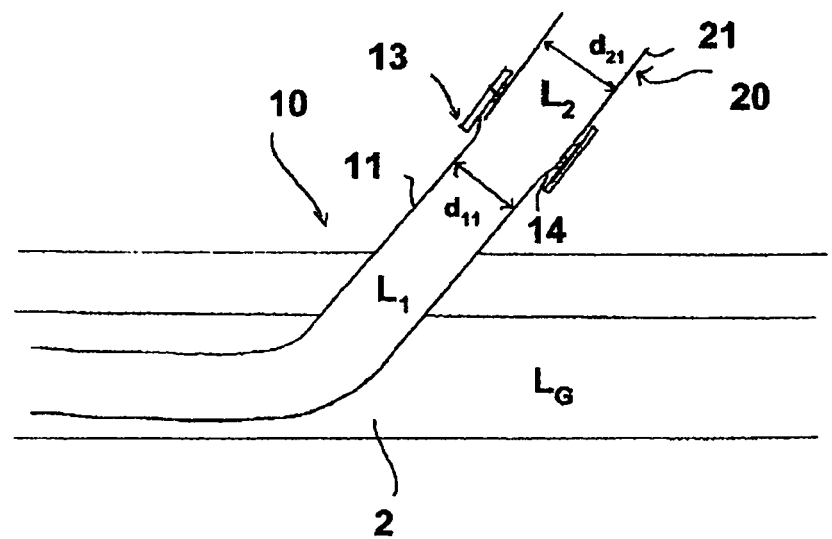
FIG. 3 shows an embodiment of the invention comprising a first sheath and a second sheath.

In the illustration of FIG. 3, the first sheath 10 of FIG. 2 is coupled to a second sheath 20. Only a tubular section 21, which defines a lumen 12 having an inside diameter d21, is shown of the second sheath 20. The outside diameter of the distal end of the second sheath 20 is such that it can be inserted into the sheath housing 13. However, the inside diameter d21 is larger than the inside diameter d11.

A pump, which is not shown and present in the lumen L2, can now be transferred into the first sheath lumen L1 from the second sheath lumen L2 by pressing. The pump is then transported through the first sheath lumen L1 to the site in the vascular system where the pump is intended to effect the action thereof. The pump can either be guided on a guide wire for this purpose, or it can be introduced without guide wire through the first sheath lumen. The first sheath can be advanced distally to the site of use of the pump before the pump is pushed out, so as to protect the pump and the vascular walls as well as the shaft catheter.

A possible embodiment of a pump 30 will be described in more detail based on FIG. 4. The pump 30 comprises a distal pump unit 31 and a shaft catheter 32, which adjoins the proximal end of the distal pump unit 31. At the proximal end, which is not shown, the shaft catheter 32 comprises a coupling for coupling the shaft catheter 32 to a drive element. The drive element can be disposed outside the patient's body and causes a flexible shaft extending in the shaft catheter 32 to rotate, which in turn drives the distal pump unit 31.

The distal pump unit comprises a pump housing 33, which is produced from intersecting nitinol struts. Portions of the nitinol housing are provided with a coating 34, which extends distally and proximally of a rotor 35 disposed in the housing 33. The rotor is connected to the shaft 36 extending through the shaft catheter 32 and thus caused to rotate. The housing and the rotor can be compressed, which is to say the pump is a self-decompressible pump. The pump deploys after the distal pump unit is pushed out at the distal end of a sheath. So as to compress the pump in preparation for the implantation, the distal pump unit is pulled into the distal end of a sheath lumen of a second sheath. The inside diameter of the sheath lumen is at least greater than the outside diameter of the shaft catheter.

The rotor may be displaceable relative to the pump housing in the axial direction, notably by means of an axial displacement of the drive shaft. However, the rotor may also be fixed in the axial direction relative to the pump housing.

The pump optionally comprises an outflow hose 37, which defines a flow duct for the pumped fluid located proximally of the rotor 35. Discharge openings, which are not shown in detail, are located at the proximal end of the outflow hose 37.

The pump can, of course, also be switched from pumping operation to suction operation, so that the pump no longer conducts fluid from the distal end to the proximal end, but vice versa.

A detailed description of a further suitable pump can be found in document EP 2 047 872 A1, for example.

The function of the system shall now be described based on FIGS. 5 to 9.

Figure 4:
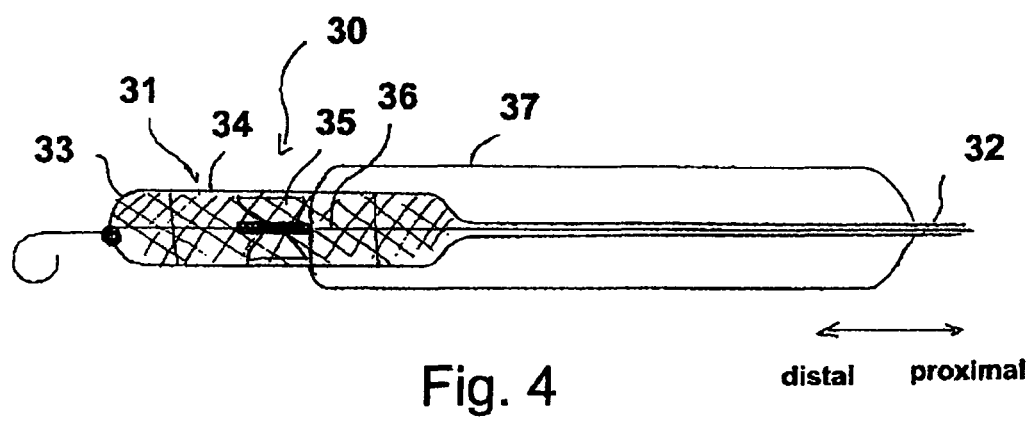
FIG. 4 shows an embodiment of a pump.
Figure 5:
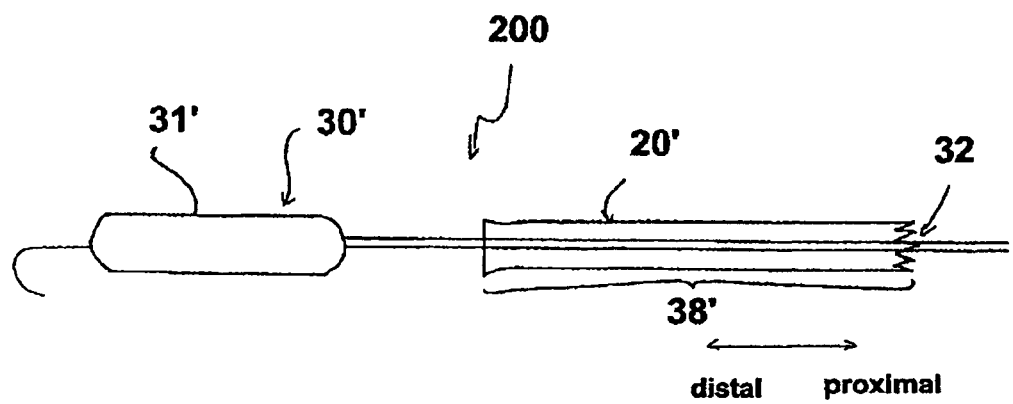
FIG. 5 shows a second sheath comprising a pump extracted therefrom.

FIG. 5 shows a pump 30', which substantially corresponds to the pump 30 of FIG. 4. To simplify matters, details of the pump are not shown. Only the bellied housing and the "pigtail" located distal of the bellied housing are shown, the pigtail preventing the heart pump from being suctioned against the cardiac wall. The shaft catheter 32' runs proximal of the distal pump unit 31'. A second sheath 20' is provided, which encloses a region 38' of the shaft catheter 32' and comprises a lumen L2, the inside diameter d21 of which is smaller than the diameter of the distal pump unit 31' when it is deployed.

The pump 30' shown in FIG. 5 is a compressible pump, which is to say the distal pump unit 31', which comprises the pump housing and the rotor located therein, among other things, is designed such that it can be compressed, which is to say that the diameter thereof can be decreased. After a quality inspector or a physician, for example, has confirmed the correct function of the pump 30', such as by observing the rotational movement of the rotor unit located in the distal pump unit 31' during a test run, the distal pump unit 31' is pulled into the lumen 12 of the second sheath 20' by pulling the shaft catheter 32' in the proximal direction. By pulling the pump into the second sheath 20', bending or damage of the shaft catheter or of the shaft extending therein is prevented. The pump 30' shown in FIG. 5 and the second sheath 20' enclosing the region 38' of the shaft catheter 32' form a system 200 which allows the function of the pump 30' to be tested in due time before surgery and the pump to be compressed by pulling the distal pump unit 31' into the distal end of the second sheath 20', and thus prevent damage to the shaft.

Although the system can be implemented both with actively decompressible pumps and with self-decompressible pumps, it is particularly suitable for self-decompressible pumps, which is to say pumps in which the distal pump unit automatically restores the original size outside the sheath.

Figure 6:
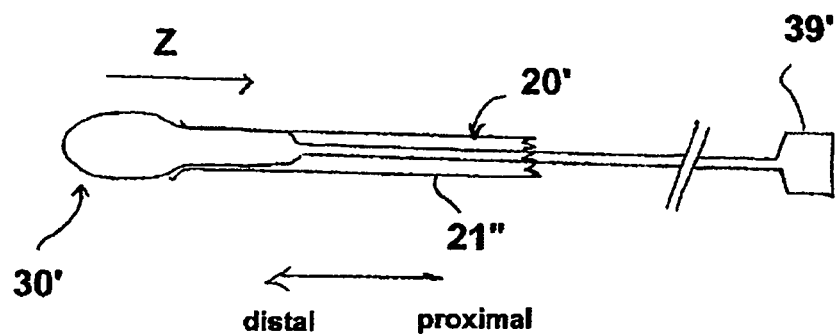
FIGS. 6, 7 show the pulling of a pump into a second sheath.

FIG. 6 shows an intermediate step when pulling the distal pump unit 30' into the lumen of the second sheath 20'. It is apparent that the distal pump unit 30' can be compressed and reduced to a smaller diameter, so that the distal pump unit 30' can be accommodated in the lumen of the second sheath 20'.

FIG. 6 further shows a coupling 39' adjoining the shaft catheter 32', the coupling allowing the shaft extending in the shaft catheter to be coupled to a drive unit. Because the coupling 39' often times has a larger outside diameter than the inside diameter of the lumen 12, the second sheath 20' is usually added from the proximal end of the shaft catheter 32' in the distal direction before the coupling 39' is mounted, so that the pump is shipped as a system 200, which is to say the pump comprising the second sheath 20' located proximal of the distal pump unit 31' and the sub-assembled coupling 39'. FIG. 6 also shows a slight expansion of the distal end of the second sheath 20'. The trumpet-shaped expansion 24' makes it easier for the distal pump unit 31' to be pulled into the lumen 12 of the second sheath 20'.

Figure 7:
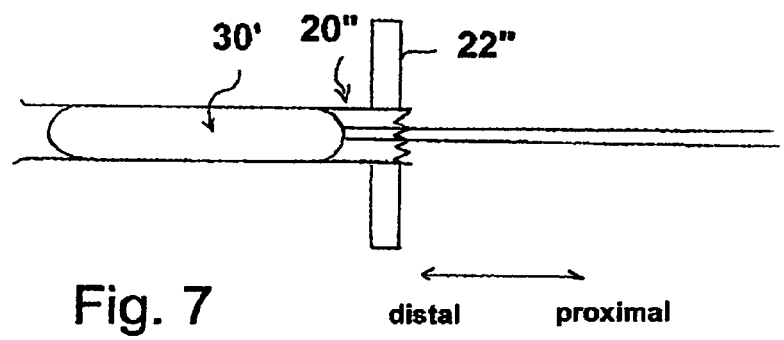

In FIG. 7 finally the distal pump unit 31' is located entirely in the lumen L2 of the second sheath 20". The second sheath 20" comprises two sub-assembled grip units 22", which allow better holding or removal of the second sheath 20" when pulling the distal pump unit 31' into the lumen L2, or subsequent tearing. If a "pigtail" is present, the same is advantageously likewise pulled into the lumen 12, so that the distal pump unit 31', together with the components of the pump located distal of the distal pump unit 31', are present in the lumen L2.

Figure 8:
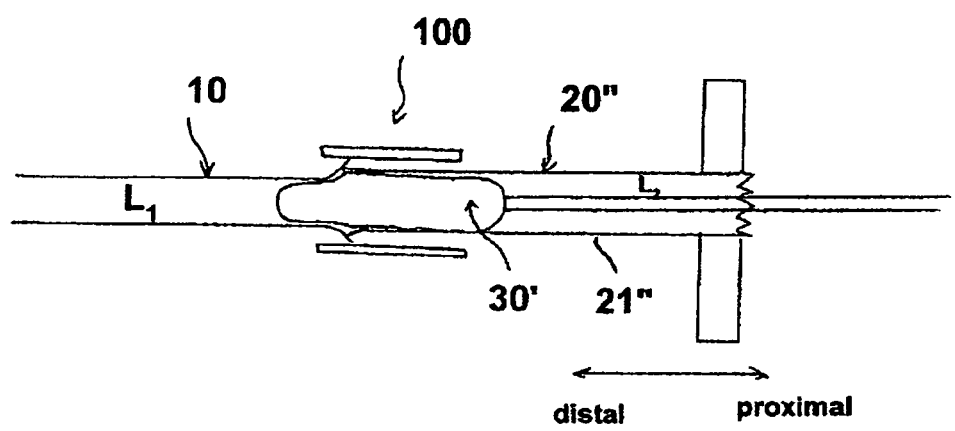
FIGS. 8, 9 show the transfer of a pump from a second sheath into a first sheath.

It is apparent from FIG. 8 how the system 200 comprising the pump 30' and second sheath 20" is combined in an operative connection with the first sheath 10 to form a system 100. First, the distal end of the second sheath 20" is inserted into the sheath housing of the first sheath 10. As soon as the distal tip of the second sheath 20" is seated against the mouth of the tubular section of the first sheath 10, the pump is transferred from the second sheath 20' into the first sheath 10' by pushing the pump in the distal direction, the pushing taking place by pushing of the shaft catheter 32'. The diameter of the distal pump unit 31' is thus reduced further to the inside diameter d11 of the lumen L1.

Figure 9:
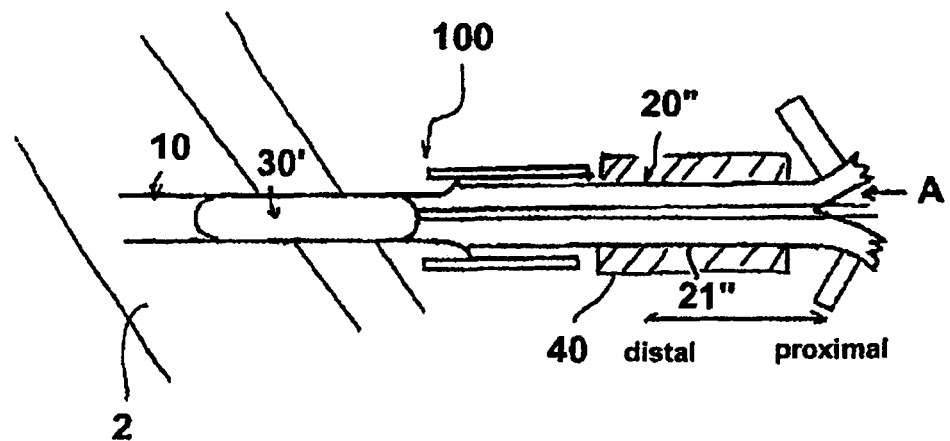

FIG. 9 shows the subsequent step, in which the distal pump unit 31' is located entirely in the lumen L1 of the first sheath 10. The fact that the distal pump unit 31' is located entirely in the lumen L1 of the first sheath 10 can be indicated, for example, by using a colored marking 50 which is applied to the outside of the shaft catheter 32'.

The second sheath 20", which is designed as a "peel-away" sheath, is then removed from the shaft catheter 32' by tearing open the peel-away sheath from the proximal end to the distal end and pulling it off the shaft catheter 32'. The directed tearing open from the proximal end to the distal end can be supported by notches A, however it is primarily based on the orientation of the molecule chains of the plastic material that is used from the proximal direction in the distal direction.

After the peel-away sheath has been removed, the pump 30' is guided further inside the lumen L1 of the first sheath 10 to the desired location.

The first sheath can optionally be advanced to the immediate vicinity of the site of use before or after the pump has been inserted using the distal sheath mouth. The first sheath has the required length to do so.

A reinforcement of the second sheath 20" is not required, in particular when pulling the distal pump unit 31' into the distal end of the second sheath lumen L2, because the risk of the shaft kinking during a pulling motion is significantly reduced.

When the pump is transferred from the second sheath to the first sheath, as shown based on FIGS. 7 to 9, the second sheath may comprise a reinforcing structure in form of an introduced wire, or the tubular section 21" of the sheath 20" is not produced from a flexible plastic material, but from a non-deformable plastic material or metal.

Another option for stabilizing the pump and the second sheath is that of holding the second sheath 20" by way of a supporting element 40 in form of a stable outer sleeve when advancing the pump 30' in the distal direction, which is to say in particular when transferring the pump 30' from the second sheath into the first sheath.

Hereafter, another possible variant of a method for inserting a pump into a left ventricle shall be described. As a preparatory measure, the pump is first filled with a sterile physiological salt solution and is thus completely freed from air. Then, the peel-away sheath located proximal of the distal pump unit is advanced to a potentially present outflow hose. The diameter of the peel-away sheath is 10 Fr, for example. After the peel-away sheath has been advanced to the outflow hose, the peel-away hose is surrounded by a sleeve-shaped element so as to hold the second sheath. The distal pump unit is then pulled into the peel-away sheath, optionally by performing a slight rotational movement, by performing a pulling motion in the proximal direction on the shaft catheter. The pump is advanced into the second sheath so far that a potentially present pigtail is likewise secured in the peel-away sheath. These steps make it possible to examine the functional capability of the pump even before surgery and to insert the pump only then into a sheath, without having to act under time pressure. For example, it is only then that the vascular system is punctured so as to insert the first sheath. However, so as to save time, it is thus also possible for an assistant to prepare the pump, while the user already carries out the puncturing.

After a 9 Fr introducer sheath, for example, has been introduced into the left ventricle, a potentially present dilator is pulled out of the introducer sheath and removed therefrom.

The pump, which is held in the peel-away sheath and which initially is, for example, enveloped by the sleeve so as to hold the second sheath, is then pushed into the sheath housing until the tip of the peel-away sheath strikes against a mechanical stop. The pump is then transferred from the peel-away sheath into the tubular section by pushing the shaft catheter. As soon as the distal pump unit has been completely transferred into the introducer sheath, as can be verified based on an optical marking on the catheter shaft, for example, the peel-away sheath can be torn open and pulled off the shaft catheter. The pump is then advanced inside the first sheath into the left ventricle. The first sheath is subsequently pulled back out of the left ventricle, to the point where the descending aorta begins.

The positioning of the distal pump unit in the left ventricle can be controlled by way of radioscopy, for example. For this purpose, an X-ray visible marking is located on the pump housing or in the vicinity thereof, for example on the catheter, or the pump housing itself is visible to X-rays. The discharge region of the pump, which is to say the discharge openings of an outflow hose, should likewise be located in the region of the ascending aorta. This can also be checked using an X-ray visible marking. A potentially present pigtail catheter tip should make contact with the tip of the left ventricle.

So as to remove the pump from the ventricle, the pump is retracted into the introducer sheath by means of a pulling force that is applied to the shaft catheter and is removed from the arterial vascular system in the compressed state. If the first sheath has already been shortened, the pump can also first be retracted a certain distance into the shaft catheter so as to compress the pump. For this purpose, the shaft catheter may comprise a pull-in funnel into which the pump can be pulled by pulling on the drive shaft. The first sheath and further remaining components are then removed from the vascular system.

The invention provides a particular advantage when a long sheath is used during the implantation and explanation of the pump. The long sheath is not only used, as is customary in the prior art, to insert the pump into an endogenous lumen, but also to guide the pump through the sheath lumen into the vicinity of the site of action. To this end it is advantageous in the medical field if the sheath has a length between 40 and 120 cm. The length is determined by the later site of action of the pump and the patient's physique.

If the pump is pulled out of the endogenous lumen together with the long sheath, bleeding of the femoral artery is stopped by means of a pressure dressing. As an alternative, the pump can be pulled out of the sheath lumen of the long sheath. A further guide wire can then be placed through the lumen of the sheath, and an element for closing the puncture can be guided via this guide wire after the sheath has been removed. This allows improved stemming of the bleeding to be achieved.

FIGS. 10 to 13 show in particular an embodiment of the first sheath according to the invention, comprising one or more clamping elements for fixing a tubular section 41 in a sheath housing 43.

Figure 10:
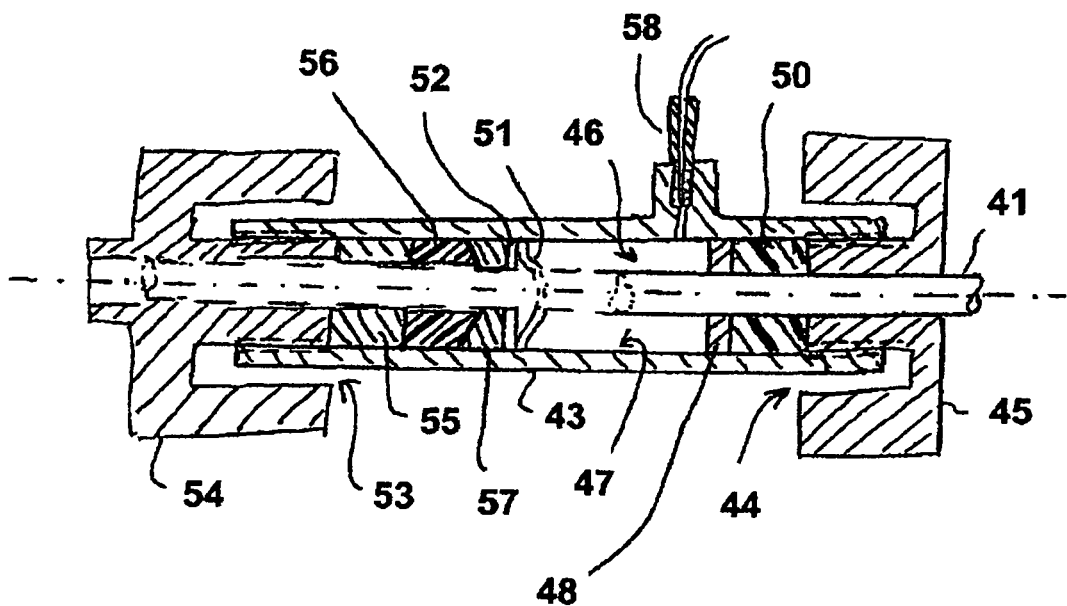
FIG. 10 is a longitudinal section through a sheath housing comprising a tubular section.

FIG. 10 shows a longitudinal section of a sheath housing 43, which substantially has the shape of a cylindrical sleeve which is closed at least at the distal end 44 facing the patient's body by a pressure screw 45. The sheath housing 43 has a continuous receiving channel 46 for a tubular section 41 of the first sheath. In the illustration of FIG. 10, coming from the patient's body, the tubular section 41 is shown continuously up to the flushing space 47 of the receiving channel 46, and then in dotted form in the proximal direction. This indicates that the tubular section 41 can be axially displaced relative to the sheath housing 43 inside the receiving channel 46 or, in other words, the sheath housing 43 can be displaced on the tubular section 41.

So as to insert a functional element, for example a pump, into the first sheath, the tubular section 41 is usually pulled out of the sheath housing 43 in the distal direction so far, or it is positioned during production of the first sheath, so that it ends approximately at the level of the first stop piece 48. A second sheath comprising a retracted pump, as described above, can be advanced up to this point, so as to then move the pump from the second sheath into the first sheath.

The first clamping element comprises elements such as the first pressure screw 45, a first clamping ring 50 made of an elastomeric material, and the first stop piece 48.

The pressure screw is screwed to the sheath housing by means of an external thread in an overlapping region with the distal end 44 of the sheath housing 43. Manually rotating the pressure screw 45 thus brings about a movement of the pressure screw in the axial direction, which results in axial compression or expansion of the clamping ring 50. During an axial compression, the clamping ring 50 tends to give way radially inward and outward so as to maintain the volume thereof and thus clamps the tubular section 41, because it experiences resistance at the proximal side by the first stop piece 48.

The tubular section 41 is thus axially fixed with respect to the sheath housing 43. This fixation can easily be released by loosening the pressure screw 45, so that the tubular section 41 is then easy to axially displace in the sheath housing 43. To this end, when it is relaxed, the clamping ring can have an inside diameter that equal to or larger than the diameter of the first sheath.

So if the tubular section 41 is first pushed as far as possible into the patient's body to allow insertion of the pump, protected by the sheath, to the site of use, for example a ventricle, the tubular section 41 is pulled out after the pump has been removed and the sheath as a whole protrudes relatively little from the patient's body. The clamping element 48, 45, 50 can then be released and the sheath housing 43 can be pushed closer to the patient's body on the tubular section 41. The tubular section 41 then extends completely through the sheath housing 43 and optionally protrudes from the same in the proximal direction. Using means which will be described in more detail hereafter, the tubular section 41 can then be severed in some regions so as to remove the excess length.

A so-called combined haemostatic valve, which is composed of a dome valve 51 and a valve plate 52, is provided inside the sheath housing 43 to provide better sealing action. The valve plate closes the sheath housing 43 if at this point neither the tubular section 41 nor a shaft catheter extends through the receiving channel 46, while the dome valve 51 is optimized so as to provide tight sealing around a strand-shaped body, for example the tubular section or a catheter.

A further pressure screw 54 is provided at the proximal end 53 of the sheath housing 43, the pressure screw basically functioning in the same manner as the first pressure screw 45 and effecting the compression of a second clamping ring 56 relative to a second mechanical stop 57 via a pressure piece 55. A special feature that should be mentioned here is that the distal end of the second clamping ring 56 has a conical shape, which favors a deformation radially inward when exerting an axial pressure by way of the pressure screw 54. The second stop 57 has a conical design in the opposite direction. However, it is also possible at this point to use a non-conical clamping ring 56, and instead one which has a rectangular or round cross-section.

FIG. 10 schematically indicates a flushing element 58, which allows the flushing space 47 to be flushed with a liquid that prevents microbes from penetrating into the patient's body through the first sheath. This flushing is particularly effective if the tubular section 41 ends in the flushing space 47 or on the distal side thereof, so that the flushing liquid can reach both the outside and the inside of the tubular section 41.

Figure 11:
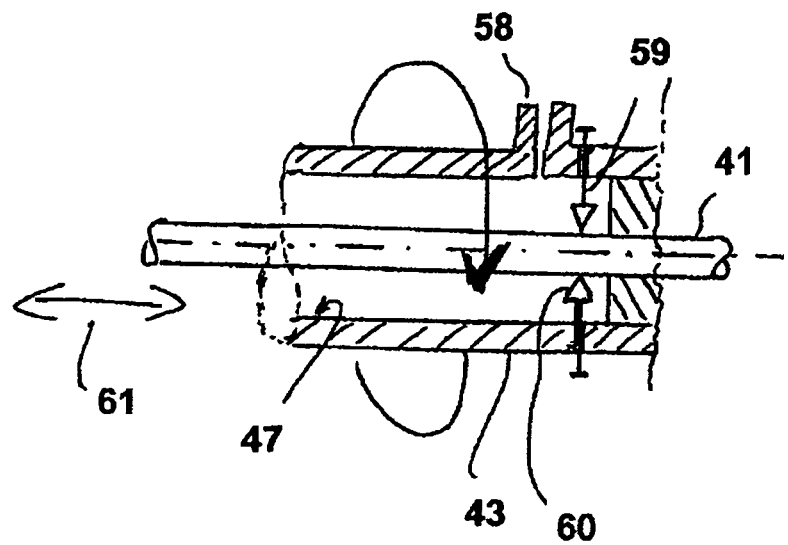
FIG. 11 is a longitudinal section through a portion of a sheath housing comprising a cutting element.

FIG. 11 shows, by way of example, the arrangement and operating principle of a cutting element according to the invention.

If no precut predetermined breaking points, or no predetermined breaking points that are predefined in another manner, for example by a predetermined molecule structure or regional weakening of the wall thickness of the tubular section 21, are provided, these can be introduced in a suitable manner when using the first sheath by way of a cutting element. In the region of the flushing space 47 of the sheath housing 43 in FIG. 11, a cutting element comprising blades 59, 60 is provided, which cuts the tubular section in the circumferential section, for example during a rotation of the sheath housing relative to the tubular section. It is also possible to introduce cuts in the axial direction.

For this purpose, the blades 59, 60 can also be disposed such that they cut in the longitudinal direction during a movement of the tubular section 41 in the axial direction, as indicated by the arrow 61. It is possible to provide blades both for cutting in the circumferential direction and a blade for cutting in the longitudinal direction.

FIG. 11 also shows that the blades 59, 60 can be moved radially toward the tubular section 41 by actuation from outside the sheath housing 43. There, a guide extending in the radial direction for one or more blade holders, a corresponding seal and a suspension can be provided, so that microbes are prevented from penetrating via this displacement element for the blades and the blades, when not actuated, radially have a distance from the tubular section 41. After use of the first sheath, it is then possible to manually apply pressure to the blades and the portion of the tubular section 41 that is not required can be cut off. A stop, which is not shown here, prevents the cutting depth from exceeding a critical dimension and causing damage to a catheter which may be present inside the sheath.

The blades shown can also form a cutting element for a second sheath.

Figure 12:
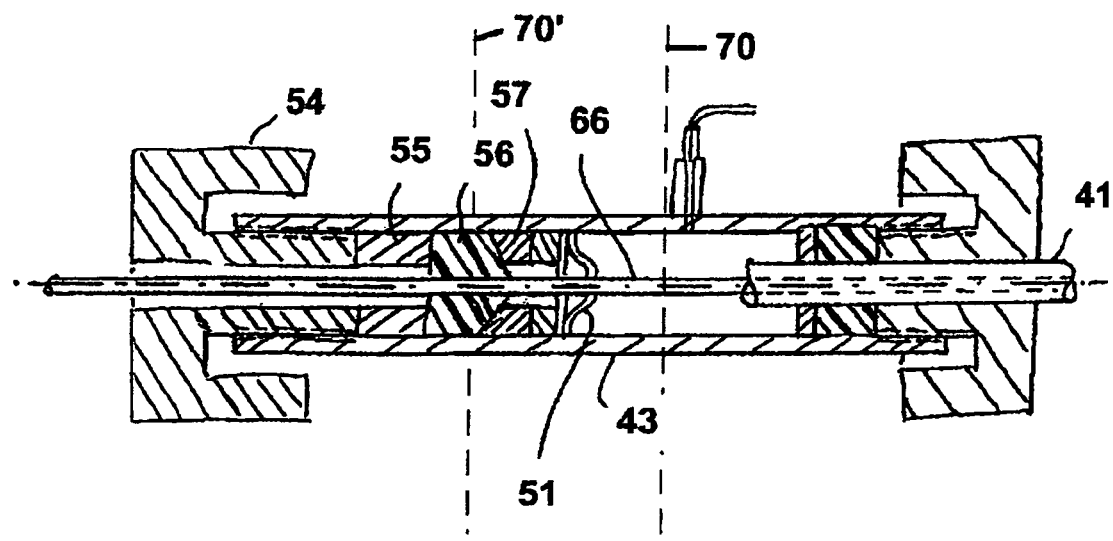
FIG. 12 is a longitudinal section through a sheath housing comprising a clamping element for the tubular section and a further clamping element.

FIG. 12 shows an advantageous use of the second clamping element on the proximal side of the sheath housing 43 after the tubular section 41 has been shortened, and a shaft catheter 61 leads out of the proximal end of the tubular section 41 and then on to a coupling element, which is not shown, for a drivable shaft of a pump and out of the sheath housing 43. The shaft catheter is sealed in the aforementioned dome seal 51, and the clamping element, together with the elements of the second pressure screw 54 and of the second clamping ring 56, which is axially compressed by the pressure piece 55 relative to the second stop 57, gives way radially inward far enough for the shaft catheter 61, which has a substantially smaller outside diameter than the tubular section 41 or a second sheath, to be clamped and in particular to be additionally sealed. Both the tubular section 41 and the shaft catheter 61 protruding therefrom can thus be fixed in the sheath housing 43.

The second clamping element is likewise suitable for fixing the second sheath with the second clamping ring 56, when inserting a second sheath into the sheath housing 43, such that the second sheath is sufficiently fixed with respect to the sheath housing 43, and notably with respect to the tubular section 41, so as to allow the shaft catheter 61 to be pushed through.

The first and second clamping rings 50, 56 can be produced from an elastomer, for example a rubber or a silicone elastomer, and can thus be fully elastic, but be deformable without being able to compress the volume. At this point, using an elastic foamed material in which some of the volume can be compressed is also conceivable.

Figure 13A:
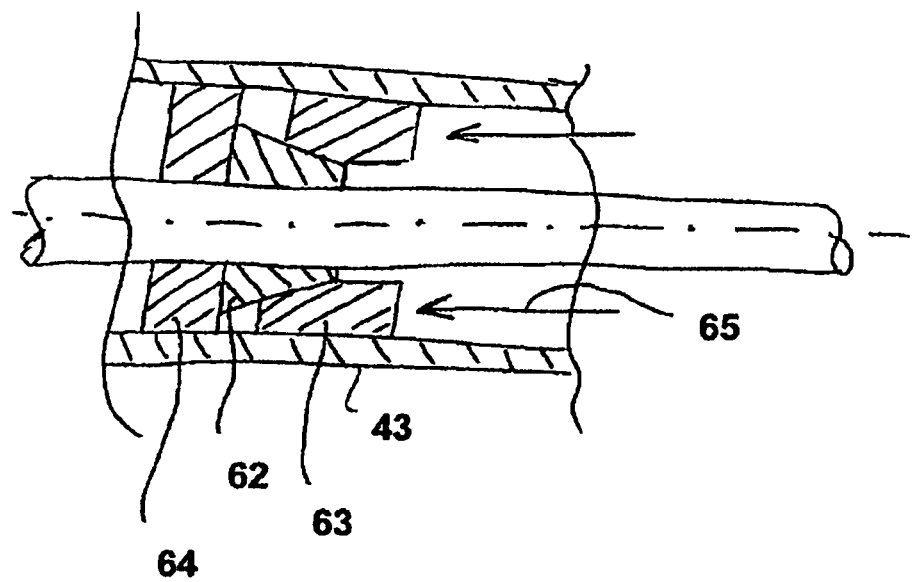
FIG. 13a is a longitudinal section through an alternative clamping ring comprising a conical pressure piece.
Figure 13B:
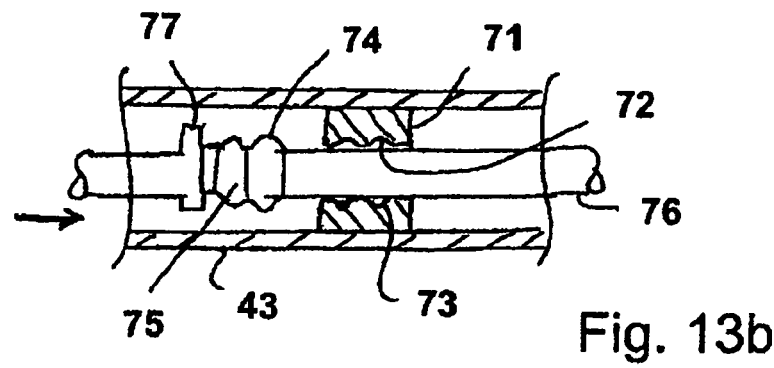
FIG. 13b is a longitudinal section through a clamped joint including lateral-walk sided notches and beads, respectively.
Figure 13C:
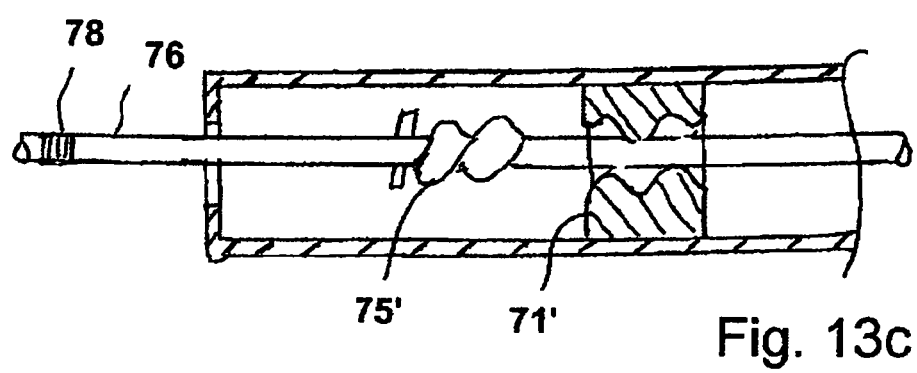
FIG. 13c is a longitudinal section including a clamped joint implemented as a threaded joint.
Figure 13D:
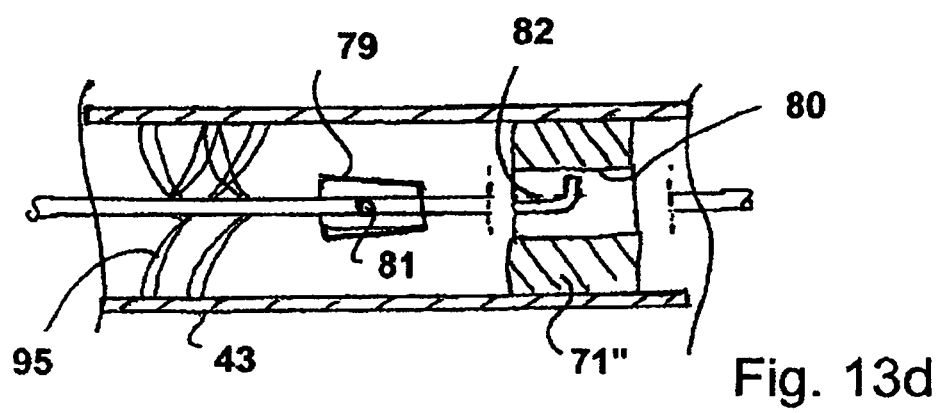
FIG. 13d is a longitudinal section including a clamped joint implemented as a conical joint in combination with a bayonet lock.
Figure 13E:
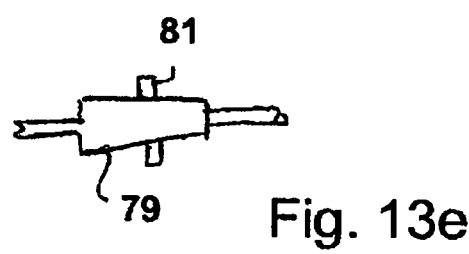
FIG. 13e is a 90°-rotated view of the taper or cone of FIG. 13d.
Figure 13F:
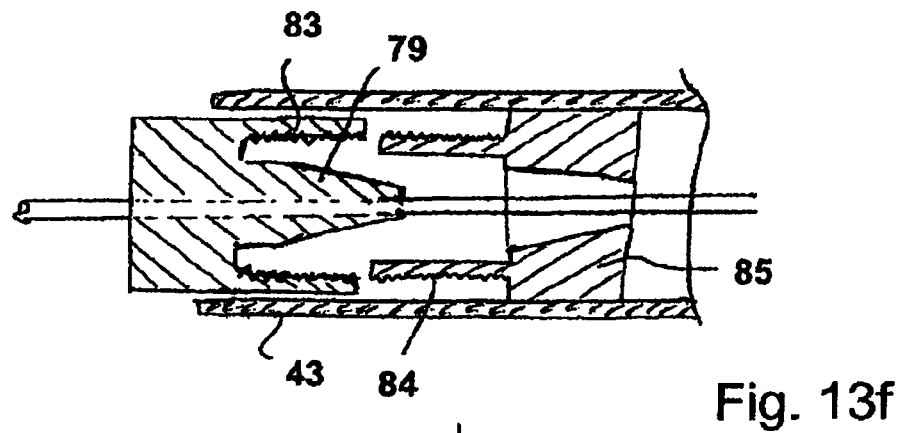
FIG. 13f is a longitudinal section of a Luer-type conical joint including a threaded joint.
Figure 13G:
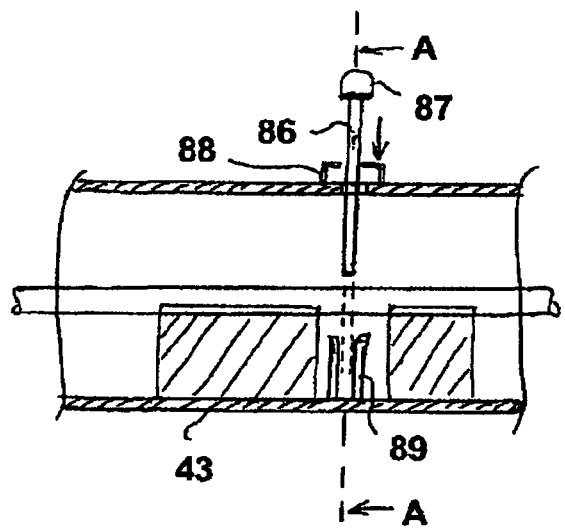
FIG. 13g is a longitudinal section of a damped joint including a transversely slidable, radially expandable spring clamp.
Figure 13H:
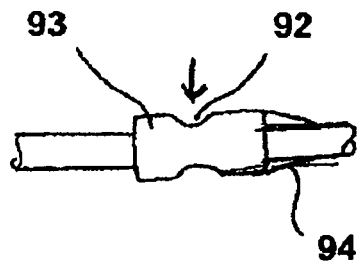
FIG. 13h is a possible configuration of the damping site area of the body to be clamped.
Figure 13I:
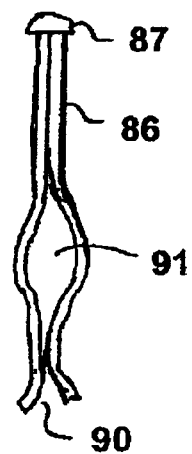
FIG. 13i is a lateral view of the spring clamp of FIG. 13g, rotated by 90° with respect to FIG. 13g.
Figure 15:
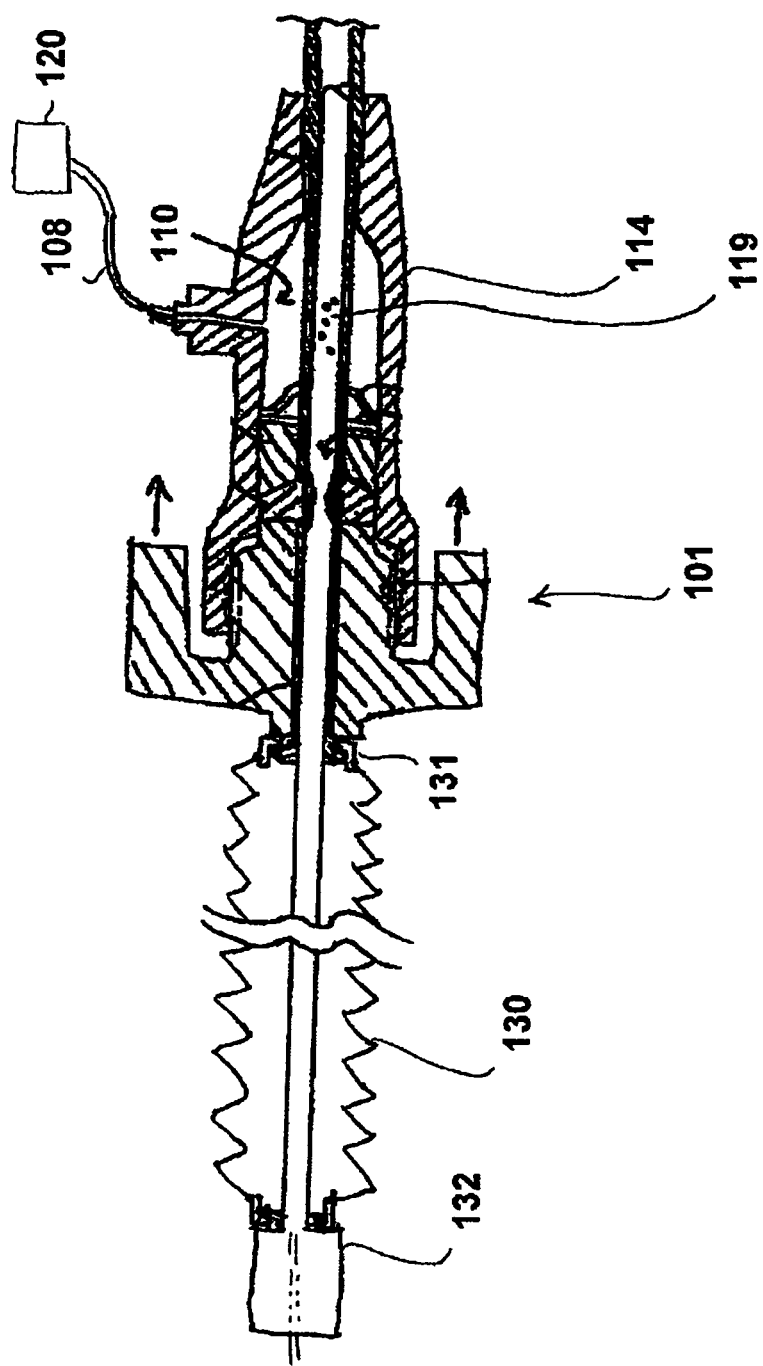
FIG. 15 shows a sterile hose part that can be fixed to a sheath device.

Instead of using a clamping ring 56 in order to establish a clamped joint it is also possible to provide a radially slidable spring clamp as shown in FIGS. 13g, 13h, 13i and explained in more detail below. A corresponding spring clamp can be provided in addition to or in place of a clamping ring. Said spring clamp can be provided in the area indicated by a broken line 70' in FIG. 12, since this area is proximal to the seal 51 and therefore the sealing requirements to be met by the sliding arrangement of the spring clamp are not particularly high.

FIG. 13a is a schematic view of another type of a clamping ring 62, which can be produced from a plastic material or a metal, for example, and in particular can be slotted and thus be radially compressible. The slotted clamping ring 62 has a conical outside contour, against which the conical contour of a pressure piece 63 pushes so as to radially compress the clamping ring as soon as an axial pressure force is exerted on the pressure piece 63 in the direction of the arrow 65, for example by a pressure screw shown above. The slotted clamping ring 62 is axially fixed by the stop piece 64.

FIG. 13*b* shows a fitting piece 71 including a passage 72, within a sheath housing, said passage 72 being provided with annular grooves and beads 73 at its cylindrical lateral surface, which fit together with grooves and beads 74 a of a matching fitting piece 75 at the body 76 to be clamped. Said matching fitting piece 75 can be inserted into said fitting piece 71 where it is elastically snapped and retained, preferably in a sealing manner. A stopper 77 prevents an excessive insertion of the body 76.

FIG. 13*c* shows an arrangement similar to FIG. 13*b*, wherein a fitting piece 71' and a matching fitting piece 75' are provided with threads, respectively, instead of concentric grooves and beads. The matching fitting piece 75' can be rotatably inserted into the fitting piece 71', however, it is also conceivable to override the thread and carry out an axial insertion. A visible mark 78 is provided at the body 76 to be clamped, in order to indicate the target position. However, a shaped mark which enables the target position to be felt or to be heard is also conceivable, or a mechanism may be provided for activating an electrical contact to put out a signal upon reaching/leaving said target position.

FIG. 13*d* shows a taper or cone 79 at the body to be clamped, which cone sealingly fits into a conical recess 80 of a fitting piece 71". Said cone 79 has one or more circumferentially arranged pins 81 which are guided within motion links 82 at the inner lateral surface of recess 80 and which serve to establish a bayonet-type lock. If the corresponding standards are met, a so-called Luer lock can be established by the joint of sealing cone and lock. Instead of said bayonet lock a threaded joint may be provided in combination with said cone system.

FIG. 13*e* shows a rotated lateral view of cone 79 with two pins 81.

FIG. 13*f* shows a cone system including a cone 79' and a threaded nut 83 surrounding the same. The threaded nut 83 can be screwed onto a thread of a pipe socket 84 which is coupled with a fitting piece 85. The fitting piece 85 is fixedly mounted within the sheath housing 43 and has an inner cone. The threaded nut 83 may also be configured as a cap nut freely rotatable with respect to the cone 79'.

FIG. 13*g* shows a sheath housing 43 including a radially guided, slidable spring clamp which can be activated via a slide button 87. A stopper 88 is provided which stops said slide button 87 at a target position. Moreover, a visible mark may be provided at the spring clamp. When the spring clamp 86 is inserted into the sheath housing 43, it enters a counter guide 89, The spring clamp has already been elastically expanded by contacting the body 76 to be clamped. To this end, it is provided with an intake opening 90 as shown in FIG. 13*i*. Upon further insertion, the receiving portion 91 encloses the body to be clamped. The latter may be provided with an annular groove or notch 92 or a sleeve 93 which includes such a groove 92. In this embodiment the clamping and sealing functions are separate at the body to be clamped.

Contrary to the functional principle described above, the clamping can also be established by completely inserting the spring clamp into the sheath housing 43 first and only then axially inserting the body to be clamped, such as a catheter or a second sheath. In this case, a conical inclined thrust surface 94 allows a sleeve 93 and the body to be clamped to be inserted into the spring clamp 86 and to be retained there.

Generally, the body to be clamped/a second sheath can also be retained within the first sheath by elastic, self-clamping lamellae, scales or teeth which tighten if the body is pulled out from the sheath. These lamellae are shown schematically on the left in FIG. 13*d* and have the reference number 95.

Figure 14:
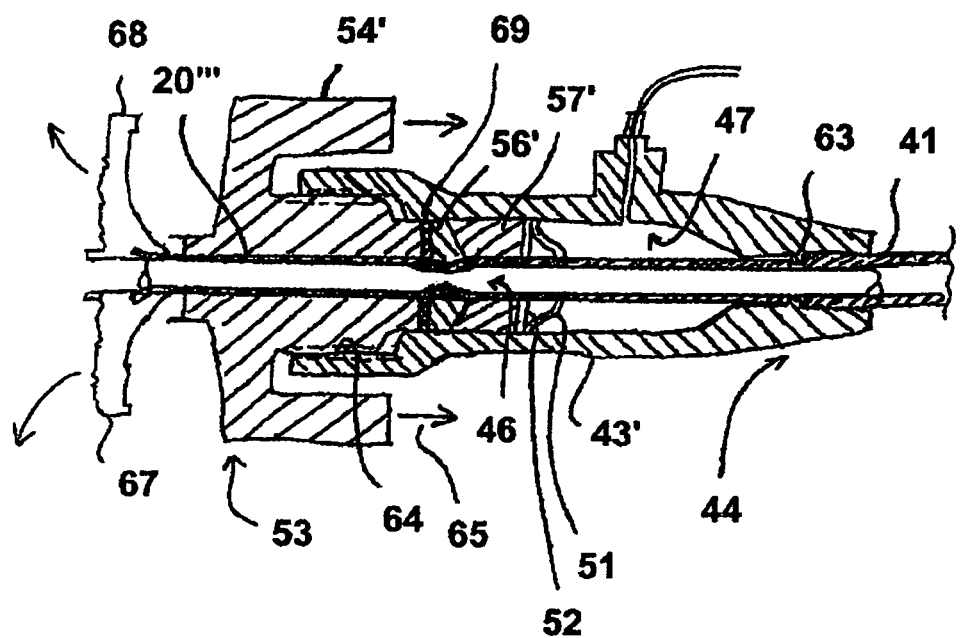
FIG. 14 is a longitudinal section through a sheath housing comprising a clamping element for a proximally introduced strand-shaped body.

FIG. 14 shows a sheath housing 43' comprising in the interior thereof a receiving channel 46 for a sheath or a catheter. At the distal end 44, the sheath housing 43' comprises a tubular section 41 which is attached to this end and which can, for example, be glued or cast into an opening of the sheath housing or be attached therein in another manner. The tubular section 41 is pushed into the opening of the sheath housing 43' up to a mechanical stop 63.

A second sheath 20''' is introduced into the receiving channel 46 from the proximal end 53 of the sheath housing 43' so far that it ends distally at the mechanical stop 63. In one embodiment, the system may also be designed so that the second sheath 20''' ends directly at the tubular section 41. For example, a functional element in the form of a pump, which is not shown, is pulled into the second sheath 20''' with a hollow catheter.

So as to transfer the catheter together with the pump from the second sheath 20''' into the tubular section 41 of the first sheath 43', 41, the two sheaths are oriented coaxially relative to one another inside the receiving channel 46, and the second sheath 20''' is fixed by means of a clamping element. The clamping element comprises an elastic clamping ring 56', which at the distal end has a conical design and is pressed against a mechanical stop 57'. For this purpose, axial pressure is exerted on the clamping ring 56' by means of a pressure screw 54', which has an external thread 64. To this end, the pressure screw 54' is screwed into the opening of the tubular portion of the sheath housing 43', so that the screw moves axially in the direction of the arrow 65.

To reduce friction between the rotating pressure screw 54' and the clamping ring 56' a slip ring 69 made of PTFE, for example, or another plastic material having good gliding properties may be provided.

The clamping ring 56' is, for example, produced from an elastomer, expands in the radial direction under axial pressure and thus clamps a strand-shaped body located in the receiving channel 46. In the clamping area of the body to be clamped one or more annular beads, webs, grooves or notches, or edges may be provided to allow a better clamping engagement. To this end, the body may also be provided with a sleeve. The second sheath 20''' has a wall thickness between 0.3 and 0.7 mm and is produced from a sufficiently stable material, so that the second sheath can be clamped under radial pressure, without the catheter extending therein being clamped at the same time. The catheter can thus be easily displaced starting from the proximal end of the second sheath 20''' into the tubular section 41. The second sheath 20''' is sealed by a combined plate and dome valve 51, 52 in a flushing space 47.

After the functional element, for example the pump, has been transferred with the catheter from the second sheath 20' into the tubular section 41, the second sheath can be torn open using the handles 67, 68 and be removed. For this purpose, the second sheath comprises a preweakened region or notching along the axial direction, or an appropriate predetermined molecule structure, which allows the second sheath to be torn open to the distal end thereof and to be removed accordingly. For the purpose of tearing the sheath open, it may be useful to release the clamping element 54', 56', 57'.

After the second sheath has been removed, the clamping element 54', 56', 57' can be clamped so far that the catheter, which has a smaller diameter, is clamped in the receiving space 46 by the further radial compression of the clamping ring 56'. The catheter, and thus a pump to be implanted, is then fixed at the distal end of the catheter in the axial direction with respect to the first sheath, and consequently with respect to the patient body.

Moldings in the sheath housing, which are not shown here, implement a respective noticeable stop for the various end positions of the pressure screw, which correspond to the various diameters to be clamped, and the user thus feels a noticeably increasing rotational resistance when actuating the screw when the respective clamping position is reached.

Following an initial phase, during which the arrangement settles mechanically and heats up to the patient's body temperature, the clamping element can be released and the catheter can be readjusted and then be re-fixed. In all areas where two cylindrical elements can be sealingly nested inside one another in the aforedescribed construction, a conical seal having a cone angle of a few degrees can advantageously be used, as is known in principle in the medical field.

The described embodiment of a sheath allows an implantable heart pump, for example, to be transferred from a second sheath, in which the pump is kept available following an initial inspection, into a first sheath leading into a patient's body without difficulty, low complexity and great reliability.

A first concept of the invention relates to a sheath device for inserting a catheter into a lumen, in particular of a patient's body, comprising a first sheath (10, 11, 13, 21, 21', 21", 41, 43) having a proximal end and a distal end, which is located in particular on the patient body side, wherein the first sheath comprises a sheath housing (13, 43) having a receiving channel (46), which hereafter is referred to as the first receiving channel, for a strand-shaped body (20', 20", 20''', 32, 66), and wherein, in extension of the first receiving channel, the sheath housing comprises a further receiving channel for receiving a tubular section, which is extends distally from the sheath housing and runs in particular coaxially relative to the first receiving channel.

A second concept of the invention relates to a sheath device according to the first concept, wherein the diameter of the first receiving channel differs from the diameter of the further receiving channel.

The diameter of the first receiving channel can be smaller or larger than the diameter of the further receiving channel. However, it is also conceivable for the diameter of the first receiving channel to substantially correspond to the diameter of the further receiving channel.

According to a third concept of the invention, a clamping element (54, 54', 55, 56, 56', 57, 57') for fixing a strand-shaped body in the first receiving channel and/or for fixing a tubular section (11, 21, 21', 21", 41) in the further receiving channel by way of clamping can be provided in the first receiving channel (46) and/or in the further receiving channel according to the first concept or the second concept of the invention.

At least one of the clamping elements (54, 54', 55, 56, 56', 57, 57') can, for example, be designed such that it selectively allows clamping of a strand-shaped body having a first diameter or of a strand-shaped body having a second diameter, wherein the first diameter is different from the second diameter.

For this purpose, for example, a clamping mechanism comprising a clamping screw can be provided, which has several preferred clamping positions. These can, for example, be implemented by various positions of the clamping screw.

According to a fourth concept of the invention, which relates to a sheath device according to the first, second or third concept, additionally a radial expansion of the first or further receiving channel containing a flushing element can be provided in the sheath housing (13, 43) in the region of the first receiving channel and/or the further receiving channel.

The flushing element can, for example, comprise one or more radial fluid connections for supplying and removing a fluid.

In the region of the radial expansion, for example at one of the axial ends thereof, additionally a valve can be provided for closing off the radial expansion in a fluid-tight manner.

The valve may comprise a valve plate and/or a dome valve.

A fifth concept of the invention relates to a sheath device for inserting a catheter into a lumen, comprising a first sheath (10, 11, 13, 21, 21', 21", 41, 43) having a proximal end and a distal end, wherein the first sheath comprises a sheath housing (13, 43) having a receiving channel (46), which hereafter is referred to as the first receiving channel, for a strand-shaped body (20', 20", 20', 32, 66), and wherein, in extension of the first receiving channel, the sheath housing comprises a further receiving channel for receiving a tubular section, and wherein a constricted channel region is provided axially between the first and second receiving channels, which connects these two channels and in which a connecting channel is provided, the diameter of which is smaller than the diameter of the further receiving channel.

Instead, it may also be provided that the diameter of the connecting channel is smaller than the diameter of the first receiving channel, or smaller than the diameter of the first and further receiving channels.

However, in addition to the constricted region, it is also possible for an expanded region comprising a flushing space to be arranged at an axial distance with respect to the receiving channels from the constricted region. The fifth concept of the invention can also be combined with any one of the first to fourth concepts.

A sixth concept of the invention relates to a sheath device according to the first or any one of the subsequent concepts (2 to 5) of the invention, wherein a cutting device comprising at least one blade is provided, which has at least one possible position, in which it radially protrudes into the first receiving channel or into the further receiving channel or into the expanded region, and more particularly into the flushing space.

For example, at least one blade that cuts in the circumferential direction of a receiving channel or a blade that cuts in the axial direction may be provided for this purpose. The respective blade(s) can each be displaceable in the radial direction with respect to the receiving channel or the expanded region between at least one cutting position and a non-cutting position, in particular a position that does not protrude into a receiving channel. The displacement can take place against the counterforce of a spring, which cooperates with the knife or a knife holder.

In addition, a fluid-tight guide channel can be provided for each of the knives.

A seventh concept of the invention relates to a sheath device according to the first or any one of the subsequent concepts (2 to 5) of the invention, comprising a tubular section that is located in the further receiving channel.

If a connecting channel according to the fifth concept is provided, the diameter thereof can correspond to the inside diameter of the tubular section (11, 21, 21', 21", 41) or it can be larger than the same.

An eighth concept of the invention relates to a sheath device according to the first or any one of the subsequent concepts (2 to 5) of the invention, comprising a tubular section that is located in the further receiving channel, wherein, if a connecting channel according to the fifth concept is provided, the diameter thereof can conically decrease starting from the first receiving channel toward the further receiving channel.

For this purpose, the cone of the connecting channel can optionally be dimensioned such that, at the site where the connecting channel abuts the further receiving channel, the diameter of the connecting channel corresponds to the inside diameter of a tubular section that is inserted at that site.

A ninth concept of the invention relates to a catheter device comprising a sheath device according to any one of the preceding concepts and comprising a catheter, which extends through the receiving channel on the inside and together with a second sleeve-shaped sheath, wherein the second sheath is fixed in a clamping element (54, 54', 55, 56, 56', 57, 57') of the first receiving channel.

A tenth concept of the invention relates to a method for inserting a catheter (32, 66) into a patient's body by means of a sheath device according to any one of the preceding concepts of the invention and by means of a second sheath (20, 20', 20", 20'''), wherein first the second sheath, together with the catheter, is inserted into the first sheath (10, 11, 13, 21, 21', 21", 41', 43), and more particularly up to a mechanical stop (63), the second sheath is then fixed by means of the clamping element (54, 54', 55, 56, 56', 57, 57'), and thereafter the catheter is transferred from the second sheath into the first sheath.

The mechanical stop can be formed by an end of the constricted channel region.

An eleventh concept of the invention relates to a method according to the ninth concept, wherein the second sheath (20, 20', 20", 20''') is removed, in particular by tearing it open or off, after the catheter has been inserted into the first sheath.

A twelfth concept of the invention relates to a method according to the ninth or tenth concept, wherein the catheter is fixed in the clamping element (54, 54', 55, 56, 56', 57, 57') after the second sheath (20, 20', 20", 20''') has been removed.

A thirteenth concept of the invention relates to a method for inserting a catheter into a patient's body by means of a sheath device according to any one of the preceding concepts of the invention, wherein a tubular section (11, 21, 21', 21", 41) is introduced into the sheath housing (13, 43) and likewise is introduced into a lumen of a patient's body, wherein then a a functional element is introduced into the lumen of the patient's body through the sheath device, wherein then the tubular section is pulled at least a certain distance out of the lumen of the patient's body, wherein the sheath housing is displaced in the distal direction relative to the tubular section, and wherein then the tubular section is fixed on the sheath housing by means of a clamping element and/or is cut off inside the sheath housing.

The invention claimed is:

1. A sheath device for inserting a catheter into a patient's body, comprising:
    a first sheath having a proximal end and a distal end, the distal end of the first sheath configured to be arranged in the patient's body during use and the proximal end of the first sheath configured to be arranged outside the patient's body, the first sheath comprising a tubular section connected to a sheath housing, the sheath housing disposed at a proximal end of the tubular section configured as a receiving channel, and wherein the sheath housing is displaceable relative to the tubular section along a longitudinal axis;
    a second sheath configured as a lumen for receiving a medical device and configured to be positioned proximal of the proximal end of the first sheath, wherein a distal end of the second sheath is positioned inside a proximal end of the sheath housing; and
    a clamping element on the receiving channel configured to clamp the second sheath in position relative to the first sheath prior to moving the medical device from the second sheath into the receiving channel;
    wherein the tubular section is configured to allow for a transfer of the medical device from the second sheath into the tubular section when the tubular section is displaced relative to the sheath housing such that the sheath housing extends proximally beyond the proximal end of the tubular section.

2. The sheath device according to claim 1, wherein the clamping element comprises an elastically radially deformable clamping ring.

3. The sheath device according to claim 2, wherein the clamping ring is produced from an elastomer.

4. The sheath device according to claim 2, wherein the clamping ring is produced from a plastic material or metal and wherein the clamping ring is slotted.

5. The sheath device according to claim 2, wherein the clamping ring can be expanded in a radially inward direction by means of a screw element acting axially relative to the receiving channel.

6. The sheath device according to claim 5, wherein the axially acting screw element exerts axial pressure on the deformable clamping ring by means of a pressure piece.

7. The sheath device according to claim 5, wherein the clamping ring is compressed radially inward by means of the axially acting screw element and an axially movable wedge body.

8. The sheath device according to claim 6 or 7, further comprising a radial expansion element of the receiving channel wherein the radial expansion element is provided on the side of the clamping ring located opposite the pressure piece or wedge body in an axial direction wherein the radial expansion element comprises a flushing element.

9. The sheath device according to claim 6 or 7, further comprising a valve sealing the receiving channel, wherein the valve is provided on the side of the clamping ring located opposite the pressure piece or wedge body in an axial direction.

10. The sheath device according to claim 7, wherein the wedge body is a ring having a wedge-shaped cross-section.

11. The sheath device according to claim 1, wherein the catheter extends through the receiving channel and wherein the catheter is fixed in the clamping element.

12. The sheath device according to claim 1, wherein the catheter extends through a receiving channel inside the second sheath, wherein the second sheath is fixed in the clamping element.

13. The sheath device of claim 1, wherein the second sheath is configured to retain the medical device before being clamped to the first sheath.

14. The sheath device of claim 1, wherein the clamping element is configured to be released to remove the second sheath from the sheath housing after the medical device has been received into the first sheath.

15. The sheath device of claim 14, wherein the clamping element is further configured to clamp the medical device in a position in the receiving channel after removal of the second sheath.

16. The sheath device of claim 1, wherein the clamping element comprises a first clamp and a second clamp, the first clamp configured to fix the second sheath relative to the first sheath, and the second clamp configured to fix the medical device in the receiving channel.

17. The sheath device of claim 1, wherein the proximal end of the tubular section widens in a trumpet-like shape.

18. The sheath device of claim 1, wherein after the transfer of the medical device the sheath housing is axially fixed relative to the tubular section.

19. The sheath device of claim 18, wherein the sheath housing is axially fixed relative to the tubular section by a pressure screw.

20. The sheath device of claim 1, wherein the tubular section protrudes from the sheath housing in the proximal direction.

* * * * *

UNITED STATES PATENT AND TRADEMARK OFFICE
CERTIFICATE OF CORRECTION

PATENT NO. : 10,709,828 B2
APPLICATION NO. : 13/261918
DATED : July 14, 2020
INVENTOR(S) : Thomas Toellner et al.

It is certified that error appears in the above-identified patent and that said Letters Patent is hereby corrected as shown below:

In the Drawings

Sheet 3 of 10, FIG. 5, Reference Numeral 32 - Delete "32" and insert --32'-- therefor.

Sheet 9 of 10, FIG. 13f, Reference Numeral 79 - Delete "79" and insert --79'-- therefor.

In the Specification

Column 5, Brief Description of the Drawings, Line 7 - Delete "lateral-walk sided" and insert --lateral-wall-sided-- therefor.

Column 5, Brief Description of the Drawings, Line 17 - Delete "damped" and insert --clamped-- therefor.

Column 5, Brief Description of the Drawings, Line 20 - Delete "damping" and insert --clamping-- therefor.

Column 6, Detailed Description of the Invention, Line 42 - Delete "12" and insert --L2-- therefor.

Column 7, Detailed Description of the Invention, Line 52 - Delete "12" and insert --L2-- therefor.

Column 8, Detailed Description of the Invention, Line 11 - Delete "12," and insert --L2,-- therefor.

Column 8, Detailed Description of the Invention, Line 21 - Delete "12" and insert --L2-- therefor.

Column 8, Detailed Description of the Invention, Line 28 - Delete "12," and insert --L2,-- therefor.

Column 8, Detailed Description of the Invention, Line 32 - Delete "how" and insert --shows-- therefor.

Column 8, Detailed Description of the Invention, Line 32 - Delete "200" and insert --100-- therefor.

Signed and Sealed this
Twenty-first Day of December, 2021

Drew Hirshfeld
*Performing the Functions and Duties of the*
*Under Secretary of Commerce for Intellectual Property and*
*Director of the United States Patent and Trademark Office*

Column 8, Detailed Description of the Invention, Line 40 - Delete "10'" and insert --10-- therefor.

Column 13, Detailed Description of the Invention, Line 55 - Delete "89," and insert --89.-- therefor.

Column 14, Detailed Description of the Invention, Line 61 - Delete "20'" and insert --20'''-- therefor.

Column 16, Detailed Description of the Invention, Line 32 - Delete "(20', 20", 20', 32, 66)," and insert --(20', 20", 20''', 32, 66),-- therefor.

Column 17, Detailed Description of the Invention, Line 36 - Delete "(20, 20', 20", 20")," and insert --(20, 20', 20", 20'''),-- therefor.

Column 17, Detailed Description of the Invention, Line 60 - Delete "a a" and insert --a-- therefor.